US008017135B1

(12) United States Patent
Hostetler et al.

(10) Patent No.: US 8,017,135 B1
(45) Date of Patent: Sep. 13, 2011

(54) LIPID-DRUG CONJUGATES FOR LOCAL THERAPY OF EYE DISEASES

(75) Inventors: Karl Y. Hostetler, Del Mar, CA (US); William R. Freeman, Del Mar, CA (US); Lingyun Cheng, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 984 days.

(21) Appl. No.: 10/770,885

(22) Filed: Feb. 2, 2004

Related U.S. Application Data

(60) Provisional application No. 60/444,228, filed on Jan. 31, 2003.

(51) Int. Cl.
*A61K 9/00* (2006.01)
(52) U.S. Cl. .................................. 424/400; 514/110
(58) Field of Classification Search .................. 424/400
See application file for complete search history.

(56) References Cited

U.S. PATENT DOCUMENTS

| | | | | |
|---|---|---|---|---|
| 5,098,443 | A * | 3/1992 | Parel et al. | 128/898 |
| 5,516,522 | A * | 5/1996 | Peyman et al. | 424/426 |
| 6,120,751 | A * | 9/2000 | Unger | 424/9.51 |

OTHER PUBLICATIONS (Lingyun Cheng, Karl Y. Hostetler, Sunan Chaidhawangul, Michael F. Gardner, James R. Beadle, Kelly S. Keefe, Germaine Bergeron-Lynn, Gregory M. Severson, Kelly A. Soules, Arthur J. Mueller, and William R. Freemanx. (herein onwards Cheng et al.). Intravitreal Toxicology and Duration of Efficacy of a Novel Antiviral Lipid Prodrug of Gancicicl.*
Lingyun Cheng, Karl Y. Hostetler, Sunan Chaidhawangul, Michael F. Gardner, James R. Beadle, Kelly S. Keefe, Germaine Bergeron-Lynn, Gregory M. Severson, Kelly A. Soules, Arthur J. Mueller, and William R. Freemanx (herein onwards Cheng et al.). Intravitreal Toxicology and Duration of Efficacy of a Novel Antiviral Lipid Prodrug of Ganciclovir.*
Cheng et al I. Investigative ophthalmology and visual science.*
Cheng et al. Investigative ophthalmology and visual science.*
Antimicrobial agents and chemotherapy by hostetler et al.*
Cundy et al.Gilead sciences.*
Ophthalmology Feb. 1983;90 (2); 121-5, abstract only and Machemer et al. (American Journal of Ophthalmology 112:159-165 Aug. 1991).*
Maghami et al. (High Myopia and Pre-eclampsia: a blinding combination, accepted Feb. 2006), 608-609 pages.*
Mayo clinic ( Stargardt's disease . . . can it be treated?..), 1 page.*
"What is AMD" 2 pages.*
(Lingyun Cheng, Karl Y. Hostetler, Sunan Chaidhawangul, Michael F. Gardner, James R. Beadle, Kelly S. Keefe, Germaine Bergeron-Lynn, Gregory M. Severson, Kelly A. Soules, Arthur J. Mueller, and William R. Freemanx. (Cheng et al.).Intravitreal Toxicology and Duration of Efficacy of a Novel Antiviral Lipid Prodrug of Ganciclovir May 2000.*

Lingyun Cheng, Karl Y. Hostetler, Sunan Chaidhawangul, Michael F. Gardner, James R. Beadle, Kelly S. Keefe, Germaine Bergeron-Lynn, Gregory M. Severson, Kelly A. Soules, Arthur J. Mueller, and William R. Freemanx (Cheng et al.). Intravitreal Toxicology and Duration of Efficacy of a Novel Antiviral Lipid Prodrug of Ganciclovir May 2000.*
Michael Barza, "Factors Affecting the Intraocular Penetration of Antibiotics: The Influence of Route, Inflammation, Animal Species and Tissue Pigmentation," *Scand. J. Infect. Dis.*, Suppl. 14, pp. 151-159, 1978.
Cheng et al., "Treatment or Prevention of Herpes Simplex Virus Retinitis with Intravitreally Injectable Crystalline 1-O-hexadecylpropanediol-3-phospho-ganciclovir"*IOVS*, vol. 43, No. 2, pp. 515-521, Feb. 2002.
Bischofberger et al., "1-[((S)-2-hydroxy-2-oxo-1,4,2-dioxaphosphorinan-5-yl)methyl] Cytosine, an Intracellular Prodrug for (S)-1-(3-hydroxy-2-phosphonylmethoxypropyl)Cytosine with Improved Therapeutic Index In Vivo" *Antimicrob. Agents Chemother.*, vol. 38, No. 10, pp. 2387-2391, Oct. 1994.
Desideri et al., "Synthesis and Anti-Rhinovirus Activity of 2-styrylchromones" *Antivir. Chem. Chemother.*, vol. 11, pp. 373-381, 2000.
Beadle et al., "Alkoxyalkyl Esters of Cidofovir and Cyclic Cidofovir Exhibit Multiple-Log Enhancement of Antiviral Activity Against Cytomegalovirus and Herpes Virus Replication in vitro," *Antimicrob. Agents Chemother.*, vol. 46, No. 8, pp. 2381-2386, Aug. 2000.
Cheng et al., "Intravitreal Toxicology in Rabbits of Two Preparations of 1-O-octadecyl-sn glycerol-3-phosphonoformate, a Sustained-Delivery Anti-CMV Drug," *Invest Ophthalmol Vis Sci.*, vol. 40, No. 7, pp. 1487-1495, Jun. 1999.
Cheng et al., "Treatment of herpes retinitis in an animal model with a sustained delivery antiviral drug, liposomal 1-O-octadecyl-SN-glycerol-3- phosphonoformate" *Retina*, vol. 19, pp. 325-331, 1999.
Lim et al:, "The Role of Gravity in Gentamicin-Induced Toxic Effects in a Rabbit Model," Acrh. Ophthalmol., vol. 112, pp. 1363-1367, Oct. 1994.
Cheng et al., "Ganciclovir Release Rates in Vitreous from Different Formulations of 1-O-hexadecylpropanediol-3-phospho-ganciclovir," *J. Ocul. Pharmacol. Ther.*, vol. 19, No. 2, 2003. Cundy et al., "Distribution and Metabolism of Intravitreal Cidofovir and Cyclic HPMPC in Rabbits," *Curr. Eye Res.*, vol. 15, pp. 569-576, 1996.
Aldern et al., "Increased Antiviral Activity of 1-O-hexadecyloxypropyl-[2-(14)C]cidofovir in MRC-5 Human Lung Fibroblasts is Explained by Unique Cellular Uptake and Metabolism," *Mol. Pharmacol.*, vol. 63; No. 3, pp. 678-681, 2003.

* cited by examiner

*Primary Examiner* — Gollamudi Kishore
*Assistant Examiner* — Snigdha Maewall
(74) *Attorney, Agent, or Firm* — DLA Piper LLP (US)

(57) ABSTRACT

Methods are provided for treating pathological conditions of ocular tissue by administering to subjects in need thereof therapeutically active complexes that include amphiphilic analogs of the therapeutically active agents. These complexes exhibit low water solubility and are isolated in either crystalline form, amorphous form, or a combination thereof, within a well-defined particle size range. Administration of such complexes of therapeutically active agents to ocular tissue results in extended release of the therapeutically active agent. Indeed, certain complexes persist for up to about 20-30 weeks or longer after intravitreal injection, thereby providing a sustained release of therapeutically active agent into the structures of the eye.

6 Claims, 12 Drawing Sheets

(a) N,N-dicyclohexyl-morpholinocarboxamidine; 1,3-dicyclohexylcarbodiimide; pyridine (b) 1-bromo-3-hexadecyloxypropane; N,N-dimethylformamide Small particle HDP-P-GCV versus large particle in PK study (2.8 μ mole dose)

Cheng L., et al. Further characterization of a novel intraocular drug delivery system

LIPID-DRUG CONJUGATES FOR LOCAL THERAPY OF EYE DISEASES

CROSS REFERENCE TO RELATED APPLICATION(S)

This application claims the benefit of priority under 35 U.S.C. §119(e) of U.S. Ser. No. 60/444,228, filed Jan. 31, 2003, the entire contents of which is incorporated herein by reference.

STATEMENT OF GOVERNMENT SUPPORT

This invention was made in part with government support under Grant Nos. EY07366 and EY11832, awarded by the National Institutes of Health, National Eye Institute. The United States government may have certain rights in this invention.

BACKGROUND OF THE INVENTION

1. Field of the Invention

The present invention relates generally to treatment of pathological conditions of the eye, and in particular to the use of lipid complexes of therapeutically active agents in treating such conditions.

2. Background Information

Direct delivery of drugs to the posterior segment of the eye by intravitreal injection of conventional nucleoside drugs, water soluble small and medium sized molecules, or intravitreal drug-containing implants has been used to treat chronic vitroretinal diseases. Compared to systemic drug administration for vitroretinal diseases, local intravitreal drug administration bypasses the blood-ocular barriers and provides a higher concentration of drug to the ocular tissue, while avoiding many of the side effects associated with systemic therapy.

Local intravitreal administration of slow-release drugs is especially desirable since frequent intravitreal administration (e.g., by injection) can cause retinal detachment and endophthalmitis. Indeed, attempts have been made to administer slow-release drugs using ocular implants. However, surgical placement and replacement of intravitreal implants can cause significant adverse effects, such as vitreous hemorrhage, retinal detachment, and infection. Intravitreal injection of a slow-release drug would be less invasive than surgery and could be reasonably repeated if the interval between injections is several weeks or longer.

To date, most intravitreally injected compounds have a short vitreous half life, which necessitates frequent injections to realize a therapeutic benefit. Liposome encapsulation of therapeutic compounds has been investigated in attempts to extend drug vitreous half life. However, liposomes may significantly decrease vitreous clarity and hence impair visual function.

Accordingly, a need exists for improved methods for delivering therapeutically active agents to the structures of the eye.

SUMMARY OF THE INVENTION

The present invention is based on the discovery that certain complexes of therapeutically active agents are effective in delivering the active agents to ocular tissue. Complexes suitable for use in the practice of invention methods exhibit low water solubility and have a well-defined particle size range, such that, when injected into ocular tissue, the complexes are dissolved or are metabolized slowly, resulting in a slow, controlled release of the therapeutically active agent into the ocular tissue.

In one embodiment, there are provided methods for treating a pathological condition of ocular tissue, including contacting a therapeutically active complex with ocular tissue, wherein the complex is formed by covalently attaching a moiety to a therapeutically active agent, resulting in a therapeutically active complex with low water solubility, thereby treating the condition.

In another embodiment, there are provided methods for treating a pathological condition of a mammalian eye, including administering to a subject in need thereof an effective amount of at least one complex of a therapeutically active agent, wherein the complex of the therapeutically active agent has low water solubility and a particle size in the range of about 10 nanometers (nm) to about 100,000 nm.

In another embodiment, there are provided methods for the slow-release delivery of a therapeutically active agent to ocular tissue, including contacting the ocular tissue with a complex of a therapeutically active agent, wherein the complex of the therapeutically active agent has low water solubility and a particle size in the range of about 10 nm to about 100,000 nm.

In a further embodiment, there are provided methods for increasing residence time of a therapeutically active agent in ocular tissue, including covalently attaching a moiety to the therapeutically active agent to form a therapeutically active complex having low water solubility, providing the complex in a particle size range of about 10 nm to about 100,000 nm, and contacting the complex with ocular tissue, thereby increasing residence time of a therapeutically active agent in ocular tissue.

DETAILED DESCRIPTION OF THE INVENTION

Figure 1A:
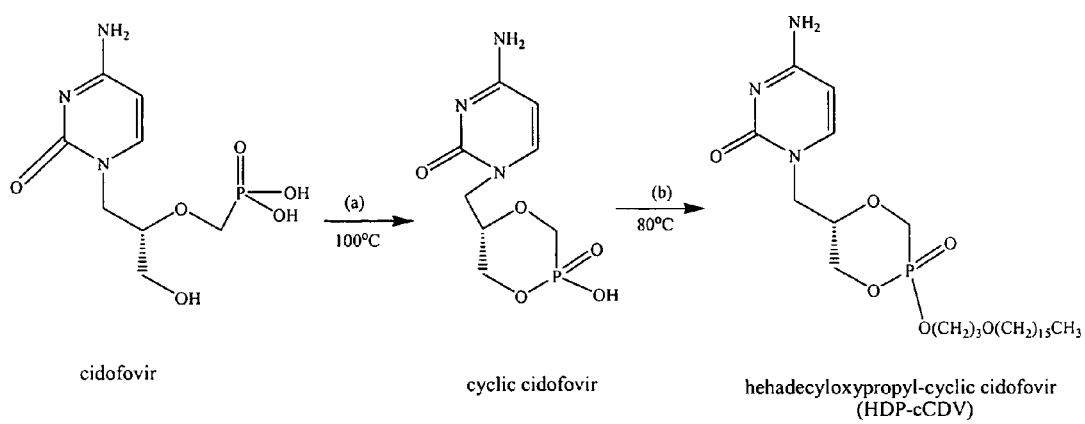
FIG. 1a illustrates the chemical structure of HDP-cCDV and the steps of its synthesis.

The present invention provides methods for treating pathological conditions of ocular tissue by administering to subjects in need thereof therapeutically active complexes that include amphiphilic analogs of the therapeutically active agents. These complexes exhibit low water solubility and are isolated in either crystalline form, amorphous form, or a combination thereof, within a well-defined particle size range. Administration of such complexes of therapeutically active agents to ocular tissue results in extended release of the therapeutically active agent. Indeed, certain complexes persist for up to about 20 to 30 weeks or longer after intravitreal injection, thereby providing a sustained release of therapeutically active agent into the structures of the eye. As used herein, the term "low water solubility", when referring to the therapeutically active complexes described herein, means that the complexes have a lower water solubility relative to the therapeutically active agents without a covalently bound amphiphilic moiety. As used herein, "amphiphilic" refers to a moiety having both a polar, water soluble group and a non-polar, water insoluble hydrocarbon chain.

In one embodiment of the invention, there are provided methods for treating a pathological condition of ocular tissue, including contacting a therapeutically active complex with ocular tissue, wherein the complex is formed by covalently attaching a moiety to a therapeutically active agent, resulting in a therapeutically active complex with low water solubility, thereby treating the condition.

Moieties contemplated for use as components of the complexes described herein are selected from a wide variety of amphiphilic moieties, such as for example, sulfates, sulfonates, phosphates, lipids, phospholipids, carboxylates, sulfosuccinates, arginine esters, cholesterol esters, carbamates, carbonates, ketals, and the like.

In some embodiments, the moieties have the following structure:

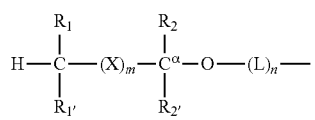

wherein:

$R_1$ and $R_1'$ are independently —H, optionally substituted —O($C_1$-$C_{24}$)alkyl, —O($C_1$-$C_{24}$)alkenyl, —O($C_1$-$C_{24}$)acyl, —S($C_1$-$C_{24}$)alkyl, —S($C_1$-$C_{24}$)alkenyl, or —S($C_1$-$C_{24}$)acyl, wherein at least one of $R_1$ and $R_1'$ are not —H, and wherein said alkenyl or acyl optionally have 1 to about 6 double bonds, $R_2$ and $R_2'$ are independently —H, optionally substituted —O($C_1$-$C_7$)alkyl, —O($C_1$-$C_7$)alkenyl, —S($C_1$-$C_7$)alkyl, —S($C_1$-$C_7$)alkenyl, —O($C_1$-$C_7$)acyl, —S($C_1$-$C_7$)acyl, —N($C_1$-$C_7$)acyl, —NH($C_1$-$C_7$)alkyl, —N(($C_1$-$C_7$)alkyl)$_2$, oxo, halogen, —$NH_2$, —OH, or —SH;

X, when present, is:

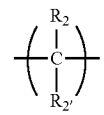

L is a valence bond or a bifunctional linking molecule of the formula -J-$(CR_2)_t$-G-, wherein t is an integer from 1 to 24, J and G are independently —O—, —S—, —C(O)O—, or —NH—, and R is —H, substituted or unsubstituted alkyl, or alkenyl;

m is an integer from 0 to 6; and n is 0 or 1.

As used herein, the term "alkyl" refers to a monovalent straight or branched chain or cyclic radical of from one to twenty-four carbon atoms, including methyl, ethyl, n-propyl, isopropyl, n-butyl, isobutyl, tert-butyl, n-hexyl, and the like.

As used herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As used herein, "alkenyl" refers to straight or branched chain hydrocarbyl groups having one or more carbon-carbon double bonds, and having in the range of about 2 up to 24 carbon atoms, and "substituted alkenyl" refers to alkenyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic groups containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As used herein, the term "bond" or "valence bond" refers to a linkage between atoms consisting of an electron pair.

In certain embodiments, m=0, 1 or 2. In these embodiments, $R_2$ and $R_2'$ can be H, and the complexes are then ethanediol, propanediol or butanediol derivatives of the therapeutically active agents. An exemplary ethanediol complex has the structure

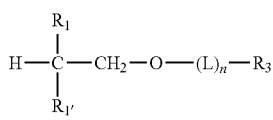

wherein $R_1$, $R_1'$, L, and n are as defined above, and $R_3$ is the therapeutically active agent.

An exemplary propanediol complex has the structure:

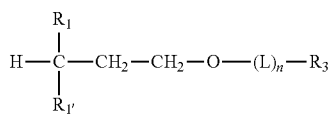

wherein m=1 and $R_1$, $R_1'$, L and n are as defined above in the general formula, and $R_3$ is the therapeutically active agent. An example of a therapeutically active complex having this structure is 1-O-hexadecyloxypropyl-phospho-arabinofuranosylguanosine (HDP-P-Ara-G).

An exemplary glycerol complex has the structure:

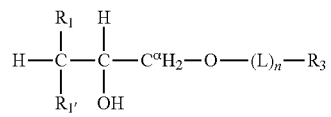

wherein m=1, $R_2$=H, $R_2'$=OH, and $R_2$ and $R_2'$ on $C^\alpha$ are both —H. Glycerol is an optically active molecule. Using the stereospecific numbering convention for glycerol, the sn-3 position is the position which is phosphorylated by glycerol kinase. In complexes of the invention having a glycerol residue, the $-(L)_n-R_3$ moiety may be joined at either the sn-3 or sn-1 position of glycerol.

A wide variety of therapeutically active agents are contemplated for use in the practice of the invention. The therapeutic agent can be selected from agents that are antineoplastic, antimitotic, antiinflammatory, antiplatelet, antiallergic, anticoagulant, anti-apoptotic, anti-necrotic, antifibrin, antithrombin, antiproliferative, antioxidant, antimigratory, antiextracellular matrix deposition, pro-apoptotic, nitric oxide donor, anti-angiogenic (e.g., angiostatin, endostatin or thrombospondin), pro-angiogenic, pro-arteriogenic, neuroprotective substances and combinations thereof. Optionally, more than one therapeutic agent as described herein can be administered to a subject. Alternatively, a therapeutic agent as described herein can be administered with a conventional agent (e.g., not modified as described herein) to achieve a therapeutic effect.

Angiogenic substances should be understood to broadly include any proteins, peptides, and small molecules and other substances that promote, stimulate or cause therapeutic angiogenesis. One of ordinary skill in the art is familiar with methods used to determine the angiogenic or arteriogenic activity of a substance, examples of which include the use of rabbit hind limb ischemia models and pig ameroid constrictor models. Representative examples of angiogenic substances include vascular endothelial growth factor (VEGF) in any of its multiple isoforms, fibroblast growth factors, monocyte chemoattractant protein 1 (MCP-1), transforming growth factor beta (TGF-beta) in any of its multiple isoforms, transforming growth factor alpha (TGF-alpha), lipid factors, hypoxia-inducible factor 1-alpha (HIF-1-alpha), PR39, del 1, nicotine, insulin-like growth factors, placental growth factor (PlGF), hepatocyte growth factor (HGF), estrogen, follistatin, proliferin, prostaglandin E1, prostaglandin E2, cytokines, tumor necrosis factor (TNF-alpha), erythropoietin, granulocyte colony-stimulating factor (G-CSF), granulocyte macrophage colony-stimulating factor (GM-CSF), angiogenin, and hormones.

Such agents include, for example, antiviral nucleosides and anti-neoplastic nucleosides. Exemplary antiviral nucleosides include adefovir, ganciclovir, cidofovir, cyclic cidofovir, tenofovir, and the like. The antiviral nucleoside may also be a derivative of azidothymidine (AZT).

Exemplary anti-neoplastic nucleosides include 2-chlorodeoxyadenosine, 1-β-D-arabinofuranosyl-cytidine (cytarabine, ara-C), fluorouridine, fluorodeoxyuridine (floxuridine), gemcitabine, cladribine, fludarabine, pentostatin (2'-deoxycoformycin), 6-mercaptopurine, 6-thioguanine, and substituted or unsubstituted 1-β-D-arabinofuranosyl-guanine (ara-G), 1-β-D-arabinofuranosyl-adenosine (ara-A), 1-β-D-arabinofuranosyl-uridine (ara-U), and the like.

Other agents that may be utilized as therapeutic agents of the invention include cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay.

The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

In other embodiments, antibodies are included as therapeutic agents in the methods of the invention, including functional fragments thereof. "Antibodies" as used herein includes polyclonal and monoclonal antibodies, chimeric, single chain, and humanized antibodies, as well as Fab fragments, including the products of an Fab or other immunoglobulin expression library.

Antibodies which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature*, 256:495, 1975). The term antibody as used in this invention is meant to include intact molecules as well as fragments thereof, such as Fab and $F(ab')_2$, Fv and SCA fragments which are capable of binding an epitopic determinant on a protein of interest.

An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An $(Fab')_2$ fragment of an antibody can be obtained by treating a whole antibody molecule with the enzyme pepsin, without subsequent reduction. A $(Fab')_2$ fragment is a dimer of two Fab' fragments, held together by two disulfide bonds.

An Fv fragment is defined as a genetically engineered fragment containing the variable region of a light chain and the variable region of a heavy chain expressed as two chains.

A single chain antibody ("SCA") is a genetically engineered single chain molecule containing the variable region of a light chain and the variable region of a heavy chain, linked by a suitable, flexible polypeptide linker.

Therapeutic agents of the invention can be proteins, small molecules, peptides, nucleic acid molecules, fragments thereof and the like. For example, aptamers can be used as therapeutic agents of the invention. Aptamers are routinely isolated from combinatorial oligonucleotide libraries using in vitro selection methods, sometimes referred to as SELEX (Ellington, A. D. and Szostak, J. W., Nature 1990, 346, 818-822; Tuerk, C. and Gold, L., Science 1990, 249, 505-510; SELEX is a trademark of Gilead Sciences Inc., USA). Aptamers can be isolated by a simple in vitro process for virtually any target, even those that are toxic or have low immunogenicity. Aptamers have a high inhibitory potential; they tend to bind grooves and clefts on proteins and can recognize binding pockets in ways resembling small molecules. Therapeutic aptamers of the invention can be specific drug-like antagonists of protein function (e.g., VEGF). Aptamers can be chemically synthesized and modified by the methods described herein.

The complexes utilized in the methods of the invention are typically isolated in either crystalline or amorphous form. In certain other aspects, complexes containing cyclic phosphates are contemplated for use in invention methods. Complexes containing cyclic phosphates are less soluble in water than the corresponding ring-opened compounds, and therefore are particularly well-suited for use in the methods of the invention. Such compounds include, for example, 1-O-hexadecyloxypropyl-cyclic-cidofovir, 1-O-hexadecyloxypropyl-cyclic-Ara C, and the like.

The complexes can typically be isolated either in the crystalline form or as amorphous material. The particle size of the isolated compounds is generally in the range of about 10 nanometers up to about 100,000 nm. In one aspect, the particle size is in the range of about 500 nm up to about 100,000 nm. In another aspect, the particle size is in the range of about 500 nm up to about 50,000 nm. In further aspects of the invention, the complexes can be isolated as a slurry, which includes a combination of amorphous material and crystalline material. For example, it is understood that the complexes of the invention need not be isolated only as crystalline material, or only as amorphous material. Indeed, complexes isolated as combinations of amorphous material and crystalline material are contemplated for use in the methods of the invention.

Free antiviral and antiproliferative nucleosides such as cidofovir and 5-fluorouracil have very short residence times after intravitreal injection of only hours or days. However, when such antiviral and antiproliferative nucleosides are employed according to the methods of the invention, the nucleosides have intravitreal residence times in the range of about 8 weeks up to about 20 weeks.

In further embodiments, the compounds can be incorporated into nanoparticles containing components which aid in delivering therapeutic agents to tissue of interest. Such components include, for example, albumin, ethylcellulose, gelatin, casein, and the like. Such materials are well-known to those skilled in the art and are as described in "Remington: The Science and Practice of Pharmacy", 20th Edition, A. R. Gennaro, Ed., Lippincott Williams and Wilkins, Baltimore and Philadelphia, 2000.

Compounds used according to invention methods are able to bypass the blood-ocular barrier and therefore provide a higher intraocular level of therapeutically active agent than is provided by systemic administration. In addition, the general side effects that are inherently associated with systemic administration are avoided by utilizing the local administration provided by invention methods. Moreover, invention methods avoid the surgical complications associated with placing, replacing, or removing a surgical implant in ocular tissue.

Since the invention methods provide slow-release delivery of a therapeutically active agent, the complications resulting from frequent injections into ocular tissue are avoided. Finally, since invention methods do not employ liposomes, there are no deleterious effects on vitreous clarity and visual function.

A variety of pathological conditions associated with the structures of the eye can be effectively treated by the methods of the present invention. Such conditions include, for example, viral retinitis (caused by herpes group viruses such as cytomegalovirus). Other conditions that can be effectively treated include inappropriate proliferation of vascular tissues in the chamber of the eye, for example, the wet form of senile macular degeneration, diabetic proliferative retinopathy, and the like.

Therapeutically active agents contemplated for use in the methods of the invention typically have a molecular weight less than about 3,000. The therapeutically active agents also have a linking group for facile linkage to the moieties described herein. Such linking groups include, for example, —OH, —COOH, —$NH_2$, —SH, and the like.

In one aspect, the complexes employed in invention methods are lipid analogs of antiviral or antiproliferative nucleosides, and include those set forth in U.S. Pat. Nos. 5,223,263; 5,411,947; 5,484,809; 5,744,592; 5,817,638; 5,827,831; 6,448,392; European Patent No. 0350287; U.S. application Ser. No. 08/487,081; and PCT Publication No. WO 01/39724 (the entire contents of each are incorporated herein by reference). In certain aspects, the compounds include 1-O-hexadecyloxypropyl-phospho-ganciclovir, 1-O-hexadecyloxypropyl-phospho-ara-guanosine, 1-O-hexadecyloxypropyl-phosphonomethoxy-ethyl-5-fluoro-uracil, and the like.

The term "effective amount" as applied to the therapeutically active complexes of the invention is an amount that will prevent or reverse the disorders noted above. With respect to disorders associated with viral infections or inappropriate cell proliferation, e.g., cancer, the "effective amount" is determined with reference to the recommended dosages of the antiviral or anticancer parent compound. The selected dosage will vary depending on the activity of the selected compound, the route of administration, the severity of the condition being treated, and the condition and prior medical history of the patient being treated. However, it is within the skill of the art to start doses of the compound(s) at levels lower than required to achieve the desired therapeutic effect and to gradually increase the dosage until the desired effect is achieved. If desired, the effective daily dose may be divided into multiple doses for purposes of administration, for example, two to four doses per day. It will be understood, however, that the specific dose level for any particular patient will depend on a variety of factors, including the body weight, general health, diet, time, and route of administration and combination with other drugs, and the severity of the disease being treated.

Generally, the therapeutically active complexes of the present invention are dispensed in unit dosage form comprising 1% to 100% of active ingredient. The range of therapeutic dosage is from about 0.01 to about 1,000 mg/kg/day with from about 0.10 mg/kg/day to 100 mg/kg/day being preferred, when administered to patients, e.g., humans, as a drug.

Actual dosage levels of active ingredients in the pharmaceutical compositions of this invention may be varied so as to administer an amount of the active compound(s) that is effective to achieve the desired therapeutic response for a particular patient.

In further embodiments of the invention, there are provided methods for treating a pathological condition of ocular tissue, including administering to a subject in need thereof an effective amount of at least one complex of a therapeutically active agent, wherein the complex of the therapeutically active agent has low water solubility and a particle size in the range of about 10 nm to about 100,000 nm, thereby treating the pathological condition.

In another embodiment of the invention, there are provided method for the slow-release delivery of a therapeutically active agent to ocular tissue, including contacting the ocular tissue with a complex of a therapeutically active agent, wherein the complex of a therapeutically active agent has low water solubility and a particle size in the range of about 10 nm to about 100,000 nm, thereby delivering a slow-release therapeutically active agent to ocular tissue.

In still another embodiment, there are provided methods for increasing residence time of a therapeutically active agent in ocular tissue, including covalently attaching a moiety to the therapeutically active agent to form a therapeutically active complex having low water solubility, providing the analog in a particle size range of about 10 nm to about 100,000 nm, and contacting the complex with ocular tissue, thereby increasing residence time of a therapeutically active agent in ocular tissue.

The invention will now be described in greater detail by reference to the following non-limiting examples.

EXAMPLES

Example 1

Synthesis of Compounds

Hexadecylpropanediol-3-phospho-ganciclovir (HDP-P-GCV) was synthesized as previously reported.[2] To prepare a small particle formulation and eliminate the population of large particles, HDP-P-GCV was suspended in distilled water and the slurry was subjected to five passes through a microfluidizer (Microfluidics, Newton, Mass.). The slurry was then flash frozen in a 1 liter round bottom flask and lyophilized overnight to remove the water.

Unmodified HDP-P-GCV and microfluidized HDP-P-GCV were subjected to laser light scattering particle size analysis at Cirrus Pharmaceuticals, Inc., Durham, N.C. Measurements were performed using a HELOS laser diffraction instrument (Sympatec, Lawrenceville, N.J.), equipped with a R3 lens (0.5 to 175 microns).

For each measurement, approximately 100 mg of dry sample was dispersed at a feed rate of 75% using the VIBRI and RODOS attachments set at a main pressure of 4.0 bar and aventury pressure of 100 mbar. The triggering conditions were set to start measurement when channel 25 e 1% and stop when channel 25 d 0.5%. Data were analyzed using the Fraunhoffer method by mean of the WINDOX 3.2 release 4 software. HDP-cCDV: cCDV was prepared from CDV as described previously[3] except that the compound was isolated as the dicyclohexyl-morpholinocarboxamidine salt. The scheme of the synthesis is illustrated in FIG. 1. The purity (greater than 98%) of these compounds used in this study was confirmed by thin layer chromatography, nuclear magnetic resonance spectroscopy, and mass spectroscopy as reported previously.[4,5]

Example 2

Animal Studies

All procedures were adherent to the ARVO Statement for the Use of Animals in Ophthalmic and Vision Research Intravitreal pharmacokinetics of small particle formulation of HDP-P-GCV: Three rabbits received 8.85 µmoles of the drug in their right eyes and 2.8 µmoles in the left eye. 2.8 µmole was previously determined to be non toxic.[2] Vitreous sampling was performed on both eyes of each rabbit at post injection week 1, week 2, week 3, week 5, week 8, week 12, and week 15. 50 to 100 µl of vitreous fluid was aspirated and placed in a pre-weighed vial for HPLC analysis of HDP-P-GCV levels as described before. 2. Intravitreal toxicity and pharmacokinetics of HDP-cCDV: For toxicity studies, five doses (10 µg or 0.018 µmole, 55 µg or 0.1 µmole, 100 µg or 0.18 µmole, 550 µg or 1.01 µmole, 1000 µg or 1.84 µmole in 50 µl of 5% dextrose) were tested in 8 rabbits, 16 eyes for 8 weeks. One eye of each animal was injected with drug and the fellow eye was injected with 5% dextrose as the control. Before drug injection, baseline IOP and fundus examination were documented. Drug or 5% dextrose was intravitreally injected into vitreous cavity as previously described.[2] After injection, eyes were monitored with a hand held tonometer (Tonopen, Medtronic, Jacksonville, Fla.), slit-lamp, and indirect ophthalmoscope at day 3, week 1, week 2, week 3, week 5, and week 8. Any change from the baseline was documented. All animals were sacrificed at 8 weeks following the intravitreal drug injection. Before sacrifice, full field scotopic ERGs were obtained from all animals as previously described.[2] Following enucleation, globes were processed for paraffin sections and light microscopic examination as described previously.[6]

For the pharmacokinetic studies, the highest non toxic dose from the results of the toxicity studies, 100 µg/eye, was intravitreally injected into 24 eyes of 16 rabbits, and the remaining 8 eyes were injected with the same volume of 5% dextrose as control. Two animals, 3 eyes with drug and 1 eye with 5% dextrose, were used at each time point. The time points used were post-injections on day 1, day 3, week 1, week 2, week 3, week 5, week 8, and week 10. After animal sacrifice, globes were enucleated and kept on ice before freezing and dissecting. The globes were then submerged in −40 C.° 2-methylbutane in a beaker sitting in a dry ice ethanol bath for 30 seconds. The frozen globe was cut into two halves through the optic nerve and further dissected under a surgical microscope to separate the vitreous and retina. These different tissues from the same eyes were separately stored in the pre-weighed and pre-labeled glass vials. The vials were kept in −70 C for HPLC analysis. 3. HSV-1 rabbit retinitis treatment study of HDP-cCDV: For the retinitis intervention study, 72 rabbits were used, including 14 rabbits for the treatment study and 58 for the pretreatment study. Only the right eye of each rabbit was used. Ophthalmoscopic retinitis grading was performed using a previously reported method with a standardized grading scheme.[7] For the treatment study, the right eyes of 14 rabbits were intravitreally injected with 0.06 mL of a 5×10$^{-5}$ dilution of 10$^{-7.6}$ mean tissue culture infective dose (TCID 50)/mL HSV-1. When retinitis developed and reached grade 1 (earliest detected retinitis grade: 1 or 2), 5 infected eyes received 100 micrograms of HDP-cCDV in 0.1 mL 5% dextrose, 4 infected eyes received an equivalent dose of free CDV, and the other 5 infected eyes received 5% dextrose. *For the pretreatment study,* 100 μg/eye was tested. 58 rabbits were divided into four groups: the 21 day, 42 day, 68 day, and 98 day groups. 15 rabbits were used for each time point of the pretreatment study (except 13 rabbits were used for the 98 day time point). At each time point 5 rabbits received 100 micrograms (in 0.1 ml 5% dextrose) of HDP-cCDV, 5 rabbits received an equivalent dose of CDV, and 5 rabbits received 5% dextrose (for the 98 day pre-treatment only 3 rabbits were used for HDP-cCDV). The HSV-1 virus dose, injection method, and clinical retinitis grading were done as previously described.[2,7] Rabbits were killed 2 weeks after development of retinitis. Retinitis was graded on day 3, 5, 7, 9, 11, 14. Rabbits without retinitis 3 or 4 weeks after HSV-1 inoculation were sacrificed.

Figure 2:
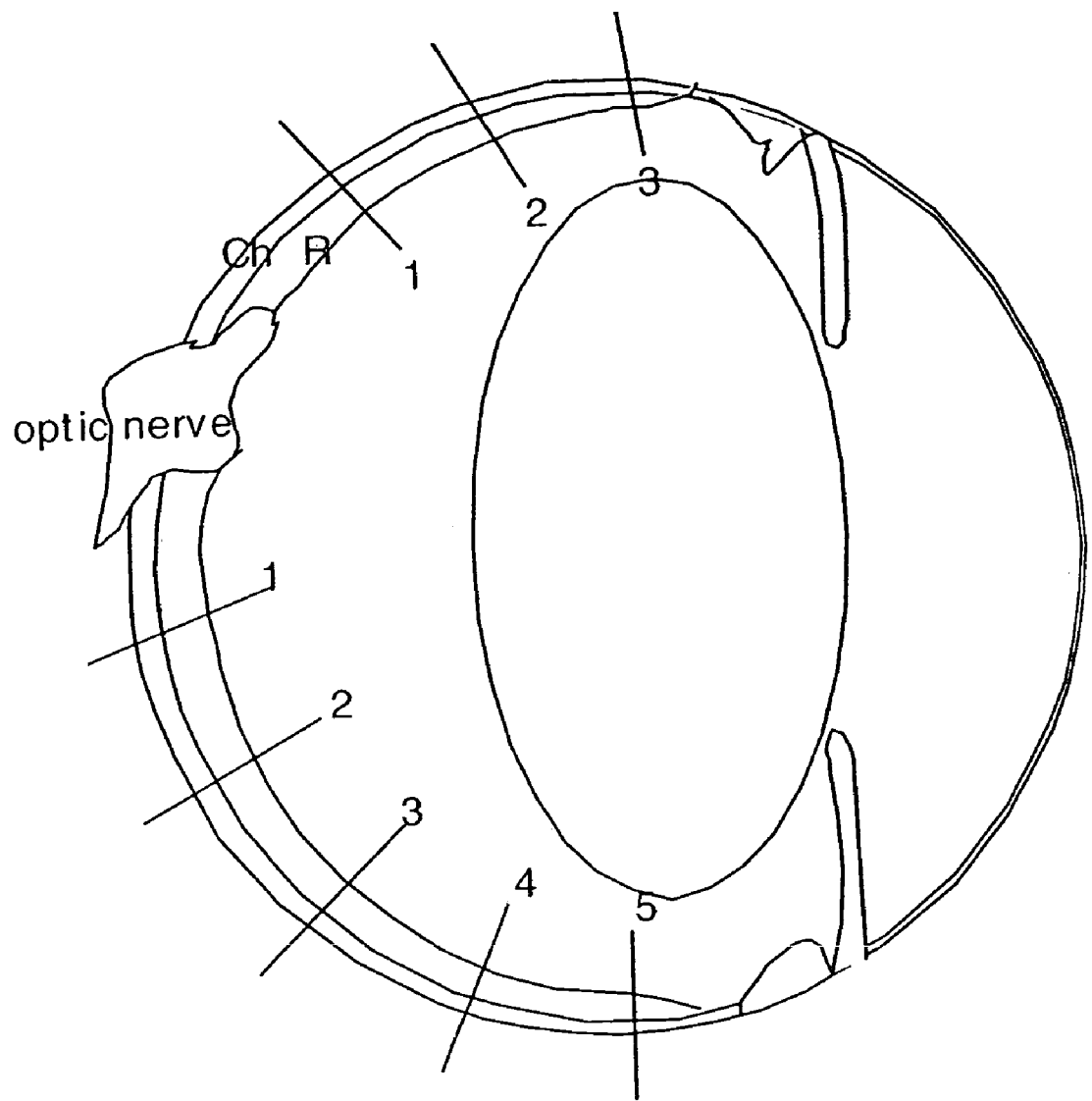
FIG. 2 illustrates a retinal section sketch for measuring retinal thickness. There are eight locations to measure retinal thickness.

4. Histologic evaluation of retinal damage and choroidal inflammation for the rabbit eyes in the treatment group. After death, globes were enucleated and were processed for light microscopy. After H&E staining, slides next to the vertical meridian were selected from each eye, one slide for each eye was chosen based on the existence of the entire retina and proximating to the optic disc. The thickness of the retina was measured at 5 locations in the inferior retina and 3 locations in the superior retina as illustrated as individual bars in FIG. 2. Thickness was measured with a reticule installed in the eyepiece of the microscope. All measurements and grading were performed under 100× magnification. Each scale unit of the reticule is equivalent to 27.8 micrometers.

Example 3

Effect of Microfluidization of HDP-P-GCV on Particle Size

Figure 3:
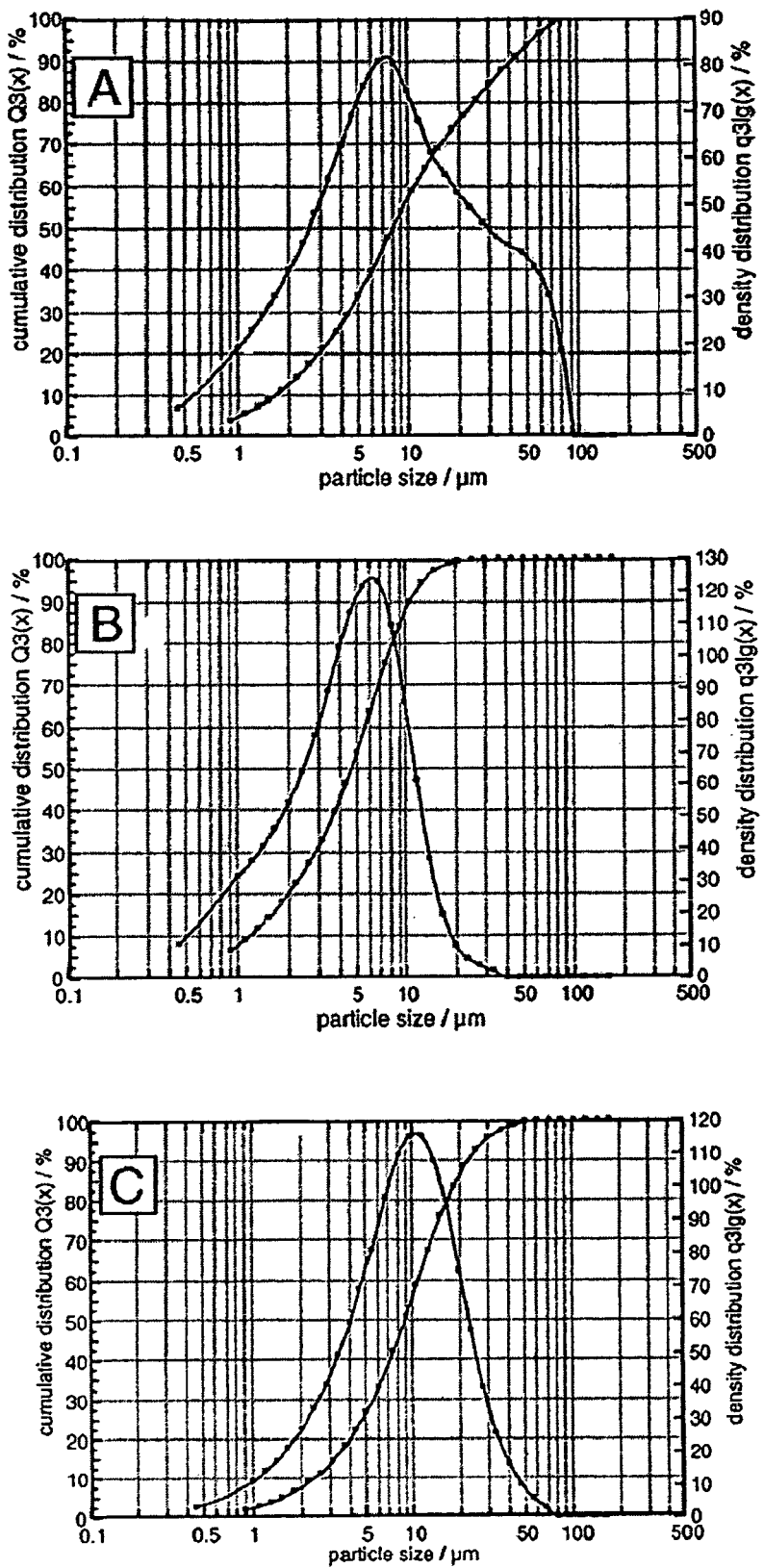
FIG. 3 depicts a Laser Light Scattering Particle Size Analysis of HDP-P-GCV and HDP-cCDV Formulations: Panel A, Unmodified HDP-P-GCV; Panel B, Microfluidized HDP-P-GCV; Panel C, HDP-cCDV.

An aqueous slurry of HDP-P-GCV was subjected to five consecutive cycles of microfluidization. After lyophilization and recovery of the powder, both the unmodified and the microfluidized HDP-P-GCV formulations were subjected to laser light scattering particle size analysis (FIG. 3). Unmodified HDP-P-GCV (Panel A) showed a bimodal distribution with a volume median diameter (×50) centered around 8.0 microns. After microfluidization (Panel B), a more monodispersed population of smaller particles is noted, having a ×50 of 4.4 microns and a 99th percentile diameter (×99) of 20 microns and a 90th percentile diameter (×90) of 10 microns. No large particles remained after microfluidization treatment. Finally, an untreated formulation of HDP-cCDV powder (Panel C) was also analyzed. This compound showed a population of particles having a ×50 of 8.9 microns.

Figure 4A:
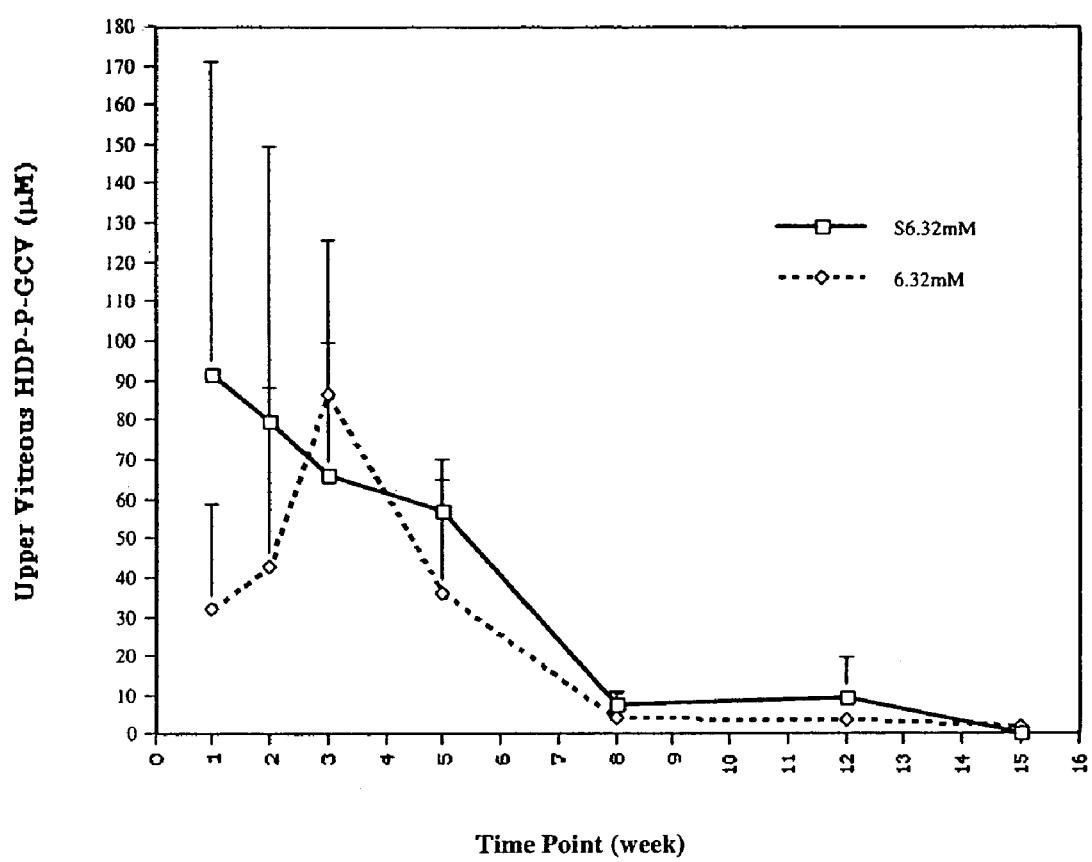
FIG. 4a illustrates micromolar concentration of HDP-P-GCV in vitreous aspirates at different time points following intravitreal injection of 8.85 μmole dose in two different particle size formulations. Data are presented as mean±standard deviation (n=3). Total AUC was calculated using JMP software (SAS Institute Inc., NC).
Figure 4B:
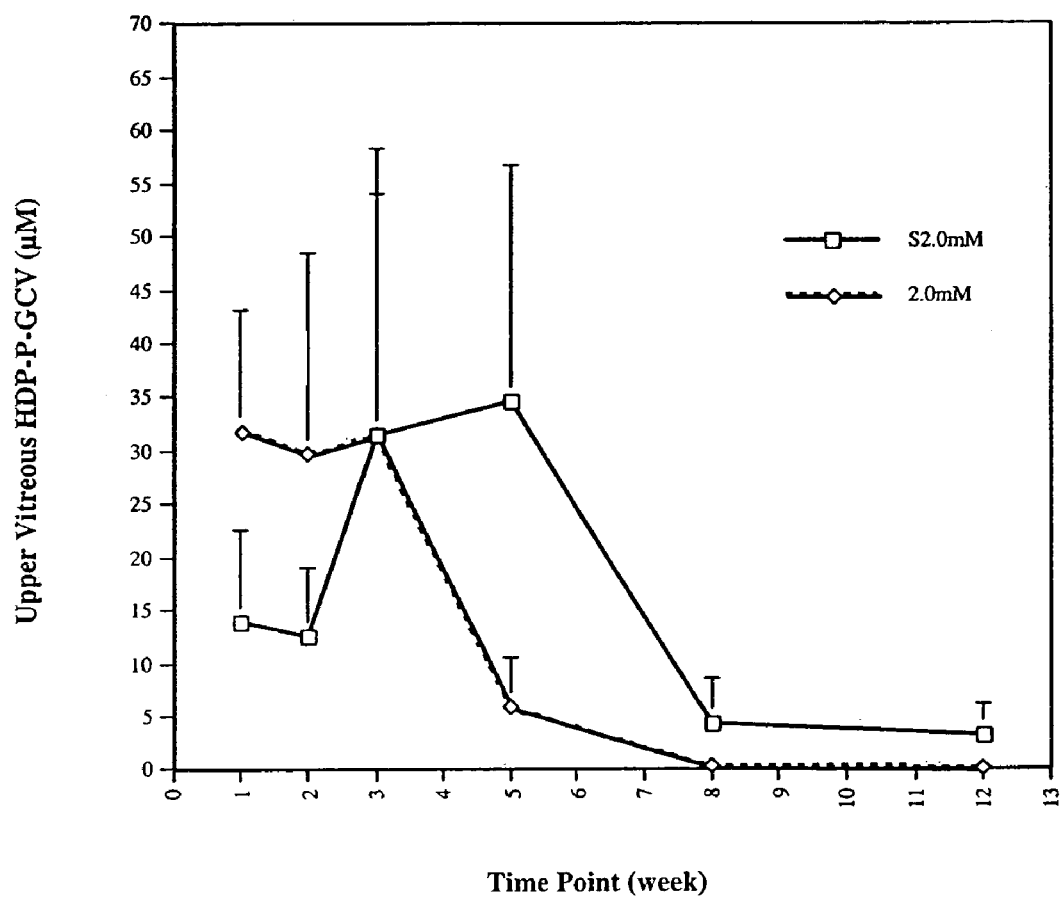
FIG. 4b illustrates micromolar concentration of HDP-P-GCV in vitreous aspirates at different time points following intravitreal injection of 2.8 μmole dose in two different particle size formulations. Data are presented as mean±standard deviation (n=3). Total AUC was calculated using JMP software (SAS Institute Inc., NC).

Intravitreal pharmacokinetics of the unmodified and microfluidized small particle formulations of HDP-P-GCV: The total area under the pharmacokinetic curve (AUC) of the microfluidized HDP-P-GCV at week 15 was 426 versus 317 for the unmodified HDP-P-GCV following an intravitreal dose of 8.85 μmoles. For the dose of 2.8 μmoles at post-injection week 12, the AUC of the microfluidized HDP-P-GCV was 193.4 versus 109.1 for the unmodified HDP-P-GCV (FIG. 4*a*, 4*b*). These results indicate that microfluidized HDP-P-GCV provides a faster release rate and higher free drug concentration in the upper vitreous (away from the injection site). This is likely due to the larger surface area of the microfluidized particles, leading to a more rapid rate of dissolution.

Figure 5:
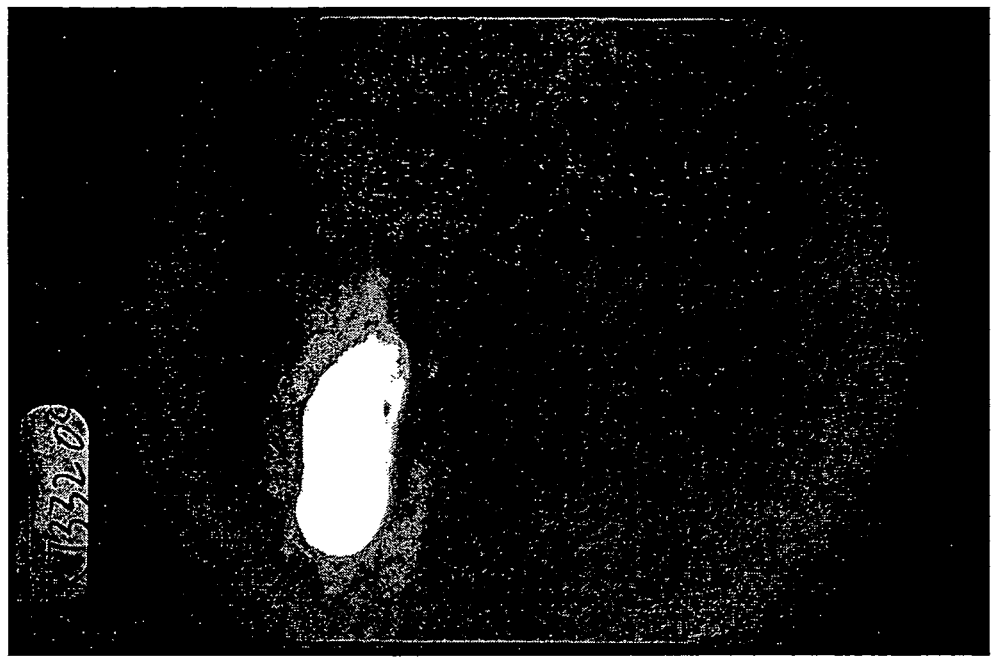
FIG. 5 is a Fundus photograph taken at week 5 following an intravitreal injection of 100 μg of crystalline HDP-cCDV into a rabbit vitreous, showing a drug depot floating in the vitreous with an estimated size of 1×1.5 disc diameters.

Intravitreal toxicity and pharmacokinetics of HDP-cCDV: The toxicity study showed that the highest non-toxic dose is 100 μg/eye. Doses of the 550 μg/eye and the 1000 μg showed local cataract and mild iritis in two eyes, one with the 550 μg dose and one with the 1000 μg dose. However, the other eye with the 550 μg dose showed no toxicity until the end of the study while the drug depot was floating in the vitreous cavity without contacting any intraocular tissue. The drug depot was still visible at the end of the study (week 8) in the eyes with 100 μg or higher doses (FIG. 5). Intraocular pressure (IOP) was measured at baseline and post-injection at day 3, week 1, week 2, week 3, week 5, and week 8 from each eye. At week 8 after drug injection, the eyes with the 100 μg dose or lower showed an average IOP of 8.7±1.0 mmHg on the right eyes and 9.8±1.1 mmHg on the left eyes (p=0.175, paired t-Test); the eyes with the 550 and the 1000 μg doses showed an average IOP of 8.7±2.1 mmHg on the right eyes and 11.3±2.3 mmHg in the left eyes (p=0.01, paired t-Test). At all other time points, IOP was not significantly different between the treated and the control eyes. ERG examination revealed that all eyes had normal ERGs, including the eye with the 1000 μg injections. Pathology study confirmed the normal retina, vitreous, and choroids in the eyes with 100 μg intravitreal injections.

Figure 6:
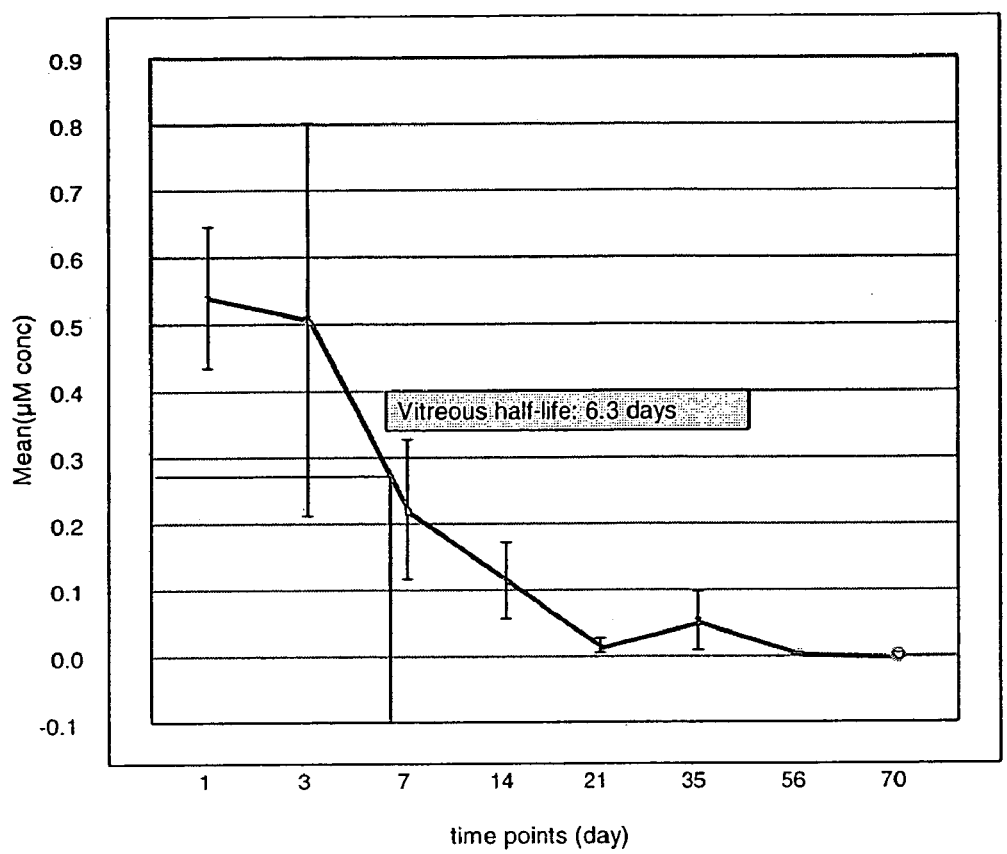
FIG. 6: is a trend plot of HDP-cCDV elimination from pharmacokinetic study of rabbit vitreous over time following 100 μg intravitreal injections. An estimated vitreous half-life was about 6.3 days. Data was presented as mean±standard deviation (n=3).

Pharmacokinetic study revealed that the whole vitreous samples showed an average concentration of 0.54 μM at post-injection day 1 and an average concentration of 0.002 μM at post-injection week 8, with an estimated vitreous half-life of 6.3 days. At the end of this experiment (post-injection week 10), HDP-cCDV was still detectable in whole vitreous samples (0.0006 μM) (FIG. 6). However, the HDP-cCDV was below the limit of detection in the retina.

Example 4

HSV-1 Retinitis Treatment Studies

Treatment Study

Out of 14 eyes of 14 rabbits that received 0.04 ml of 1×10$^{-4}$ dilution of 10$^{-7.6}$ TCID/50 HSV-1, 12 eyes developed retinitis at day 4 after virus inoculation. Rabbits were randomly divided into three groups. Retinitis scores were not significantly different among three groups before the intravitreal drug or dextrose injections (p=0.77, Kruskal-Wallis Tests). The four eyes that received the 5% dextrose solution after development of retinitis (median score of 1) progressed to complete retinitis with retinal detachment and severe vitreous cloudiness. The four eyes that received intravitreal HDP-cCDV and the 4 eyes that received cidofovir following induction of retinitis (meadian score of 1.5 and 2), showed similar clinical scores of retinitis to the 5% dextrose controls at all check time points (P>0.05, Kruskal-Wallis Tests). However, vitreous cloudiness was noticeably less severe than the control eyes. The measurement of thickness of retina from histological evaluation revealed that the thickness of the retina in the eyes with intravitreal injection of CDV and HDP-cCDV was significantly thicker than that in the 5% dextrose injected eyes (95 and 80 vs. 46 μm, P<0.05, Nonparametric Tukey-type tests). There was no significant difference between CDV and HDP-cCDV treated groups.

Example 5

Pretreatment Study

For the 3-week pretreatment study, all five rabbits that received intravitreal injection of 5% dextrose developed typical retinitis. In contrast, none of the rabbits that received the intravitreal injection of HDP-cCDV or CDV developed retinitis (Table 1). For the 47-day pretreatment, at day 7 after virus inoculation all control eyes developed retinitis with a median grade of 4. The rabbits that received CDV pretreatment all developed retinitis with a median grade of 3. In contrast, out of 5 rabbits that received HDP-cCDV pretreatment, only 2 developed grade 2 retinitis. There is a significant difference in retinitis scores between HDP-cCDV pretreated eyes and CDV pretreated eyes or control eyes (p<0.05, Nonparametric Tukey-type tests). For the 68-day HDP-cCDV pretreatment study, at day 14 following virus inoculation, only two rabbits developed grade 3 and grade 4 retinitis, the other three rabbits had complete protection from HSV-1 infection. The other two groups (10 eyes) with dextrose or CDV pretreatment all had grade 4 retinitis. The difference in retinitis scores among the three groups was very significant (P=0.0046, Kruskal-Wallis Tests) (Table 1). For the 100-day pretreatment study, one of four rabbits in the HDP-cCDV pretreated group died before virus inoculation. Among the other three rabbits, one did not develop retinitis, and the other two had grade 3 retinitis at day 9. The HDP-cCDV pretreated group had lower retinitis scores than the retinitis scores in the dextrose pretreated group (P<0.05, Nonparametric Tukey-type tests).

The data set forth herein further define the effect of particle size on the novel crystalline HDP-P-GCV intraocular drug delivery system that was reported earlier.[2] It was found that the unmodified crystalline lipid complex of GCV possesses a slow release property after intravitreal injection. It had previously been shown that HDP-GCV could prevent HSV-1 viral infection of retina for 20 weeks following a single intravitreal injection, while a single intravitreal injection of GCV provided less than one-week protection.[2] In the current study, it was demonstrated that microfluidized small particle HDP-P-GCV released a greater amount of free drug into the upper vitreous than the unmodified large particle formulation of HDP-P-GCV. This is because that small particles have a larger surface area which increases the contact surface with the dissolution medium, resulting in a higher dissolution rate than large particles. It is possible that very small amounts of the complex may diffuse from the lower to upper part of vitreous and were sampled into the vitreous tap, which may responsible for the relatively larger variation of the upper vitreous drug concentrations between individual animal eyes. Three animals per time point were used to get a mean value from which the data curve showed a clear trend and valid information. Injection of lower drug levels could eliminate the local retinal toxicity resulting from contact of drug depot with retina due to gravitational effects and positioning.[2,8] In addition, our findings suggest that controlled release could be achieved by using mixtures of different sizes of crystalline drug in an intravitreal administration. These mixtures could be designed to have release profiles tailored to treat different kinds of vitreoretinal diseases.

This novel intraocular drug delivery system was previously described using HDP-P-GCV as a prototype.[2] It was determined that the hexadecyloxypropanol moiety can be coupled to many nucleoside phosphates or phosphonates small molecule compounds to form solid hydrophobic crystals which slowly dissolve in water. The dissolved molecules enter the cells and are cleaved intracellularly by phospholipases C into hexadecyloxypropanol and the therapeutically active agent.[9] As set forth herein, the same concept and technique were used to synthesize an ether lipid ester of cyclic cidofovir, HDP-cCDV. Intravitreal injection of HDP-cCDV crystals demonstrated an ideal drug depot and clear vitreous without any toxicity in the eyes with 100 µg or lower doses. Local toxicity seen with higher doses was caused by the contact of drug depot with retina or lens. The higher dose forms a larger drug depot in vitreous, which tends to contact intraocular tissues to cause toxicity. An intraocular pressure drop associated with intravitreal injection of CDV was not observed in the eyes which received 100 µg or lower doses. The eyes with higher doses showed a mild IOP drop at the last time point (8.7±2.1 versus 11.3±2.3 mmHg, P=0.01). However, no hypotony was found. This may be due to the fact that cyclic CDV and HDP-cCDV are not picked up avidly by organic anion transporters in the ciliary body. Intravitreal pharmacokinetics showed that HDP-cCDV was still detectable at week 10 after a single intravitreal injection of 100 µg per eye. The estimated vitreous half-life for HDP-cCDV was 6.3 days, which favorably compares to 20 hours for CDV or 10 hours for cCDV.[10] The detected concentration at week 8 was 0.002 µM, which is above the $IC_{50}$ for CMV. HDP-cCDV was not detected in the retina, which could be due to low sensitivity of HPLC and fast conversion of HDP-cCDV into cCDV then into CDV by cellular phosphohydrolases. Using HDP-P-GCV, it was shown that the complex may be metabolized by participation of vitreous cells. There is little therapeutically active agent detectable when the complex was incubated with heat inactivated vitreous sample but conversion can be detected readily by native vitreous which contains cells.[9] It has been known that CDV is phosphorylated to cidofovir diphosphate, the active form of cidofovir which has a long intracellular half-life.[11] Indeed, the pretreatment studies indicated an at least 100 days pharmacologic effect against HSV-1 infection of the rabbit retina.

Example 6

Figure 1B:
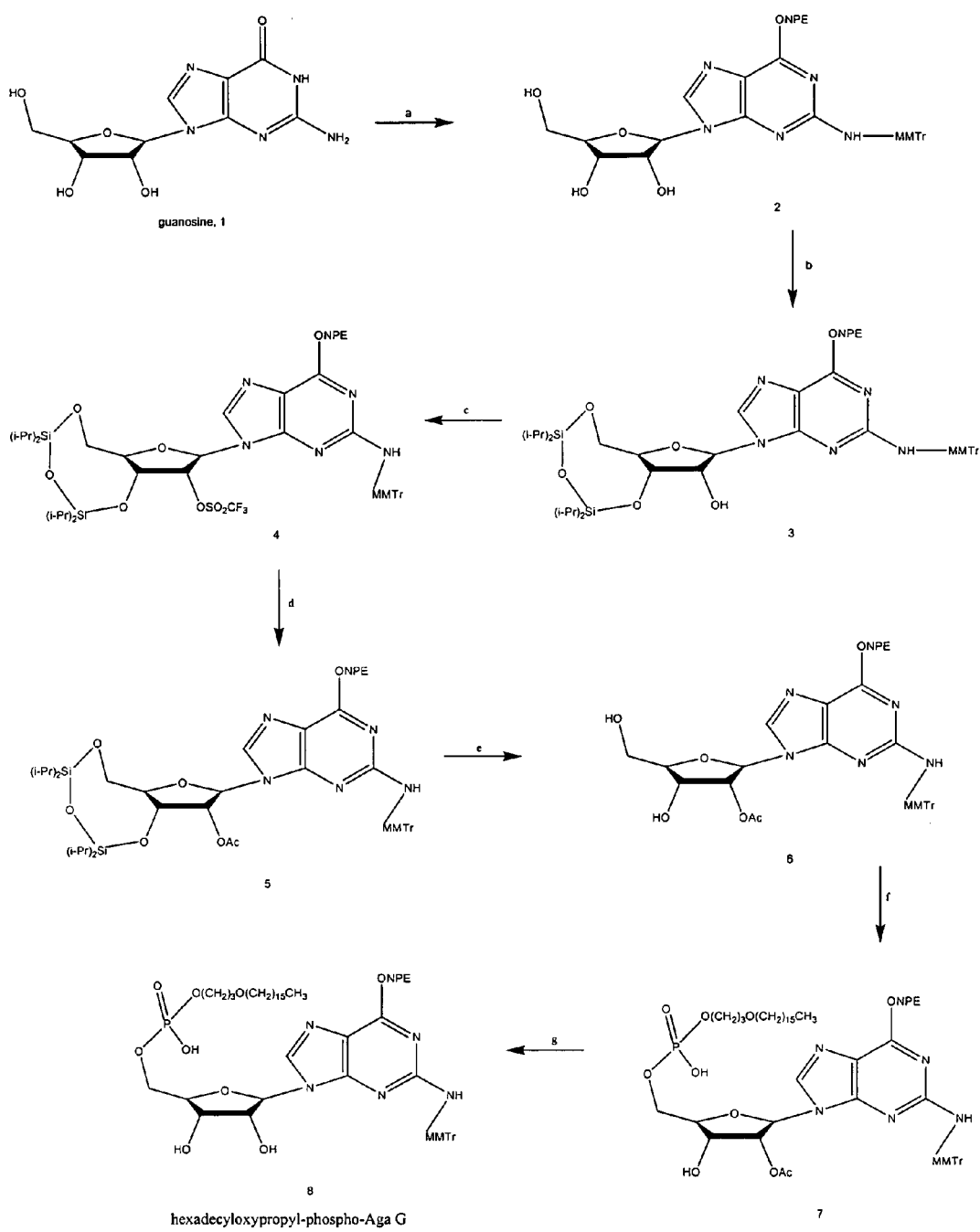
FIG. 1b illustrates the chemical structure of HDP-P-Ara-G and the steps of its synthesis.

HDP-P-Ara G: The synthesis of HDP-P-Ara G is shown in FIG. 1b. Efficient coupling of Ara G to the alkoxyalkyl phosphate required a blocked derivative of Ara G. A suitably blocked Ara G derivative (6) was obtained using a modified version of the synthesis published by Resmini and Pfleiderrer.[4] After blocking the reactive groups of guanosine, the 2' hydroxyl was converted to trifluoromethanesulfonate (4). Reaction of (4) with lithium acetate, followed by partial deblocking provided compound (6). Compound (6) was then coupled to hexadecyloxypropyl phosphate using dicyclohexylcarbodiimide as the condensing reagent. Complete deblocking afforded the target compound, HDP-P-Ara G, as a white crystalline solid.

Figure 7A:
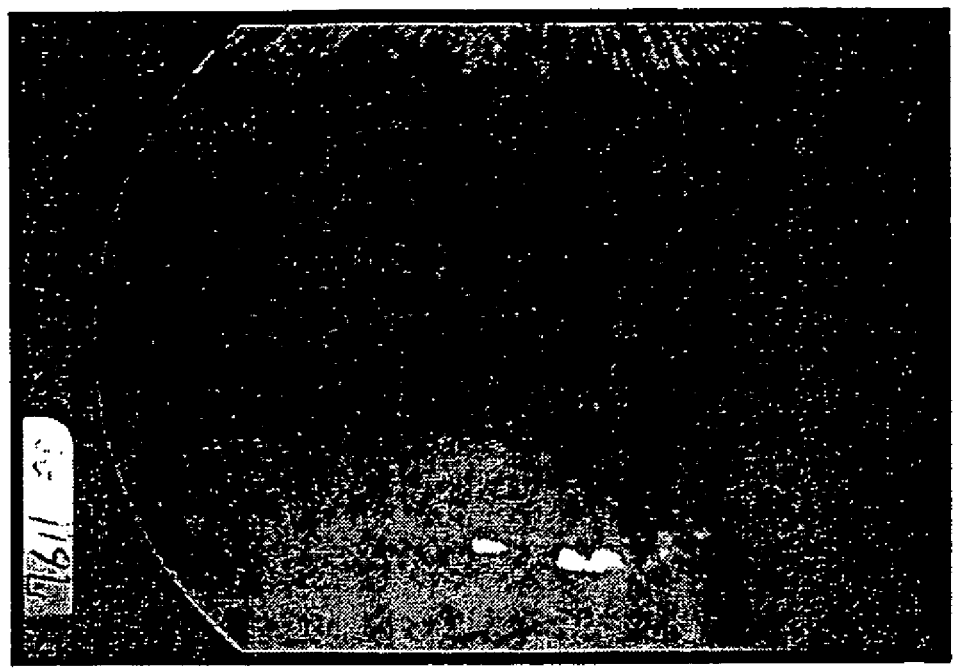
FIG. 7a illustrates a Fundus photograph taken at week 1 following an intravitreal injection of 125 µg of crystalline HDP-P-Ara G into a rabbit vitreous, showing remaining drug depot floating in the vitreous. A local retinal depigmentation area was present under the remaining drug depot.
Figure 7B:
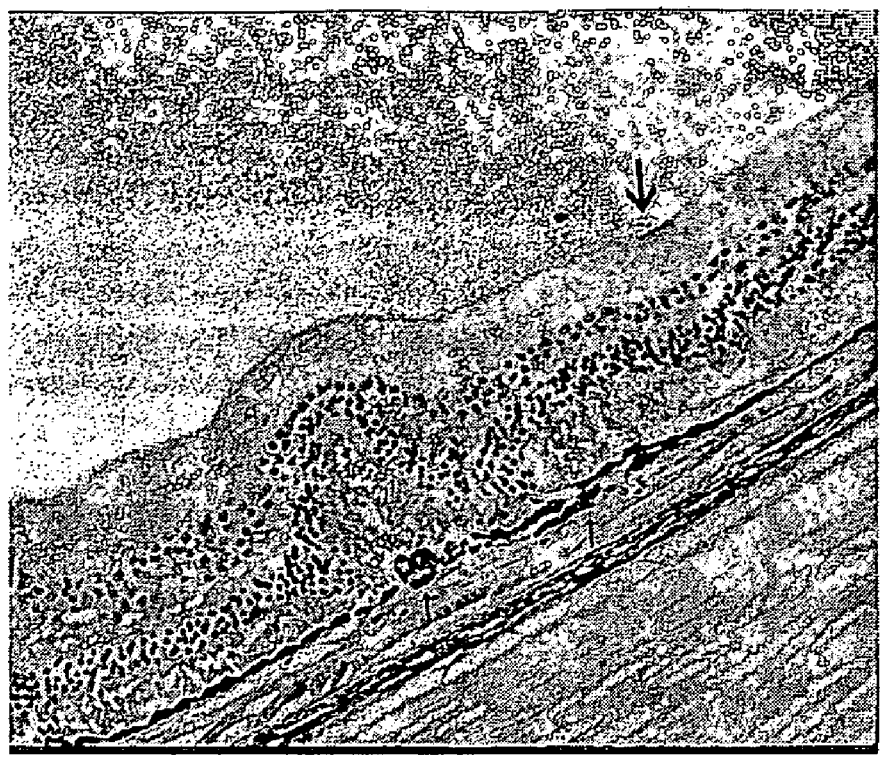
FIG. 7b is a light microscopic photograph corresponding to the clinically observed localized retinal toxicity seen in FIG. 7a, showing overall retinal edema with increased thickness (the retina left of the arrow) compared to the normal retina (the retina right of the big arrow) and retinal pigment epithelium proliferation (small arrows).
Figure 8A:
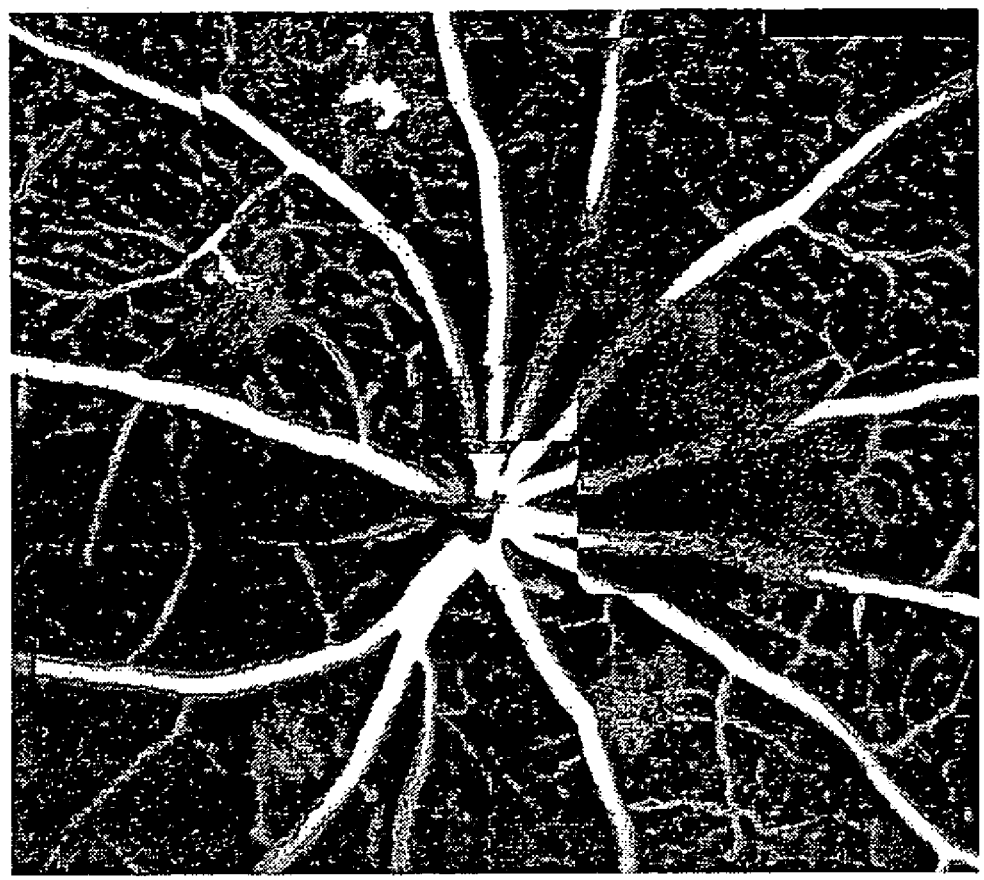
FIGS. 8a and b are fluorescein angiographs (FA) taken in a late stage (10 minutes) at 2 weeks following laser coagulation. Graph a, was from the right eye that received 3 µg HDP-P-Ara G 3 days before lasering. FA shows hyperfluorescein staining of the laser burns and one burn showed a mild leakage (arrow). Graph b was from the left eye that received 3 of 5% dextrose 3 days before lasering. FA shows obvious leakage on three burns (big arrows) and moderate leakage on two burns (small arrows).
Figure 8B:
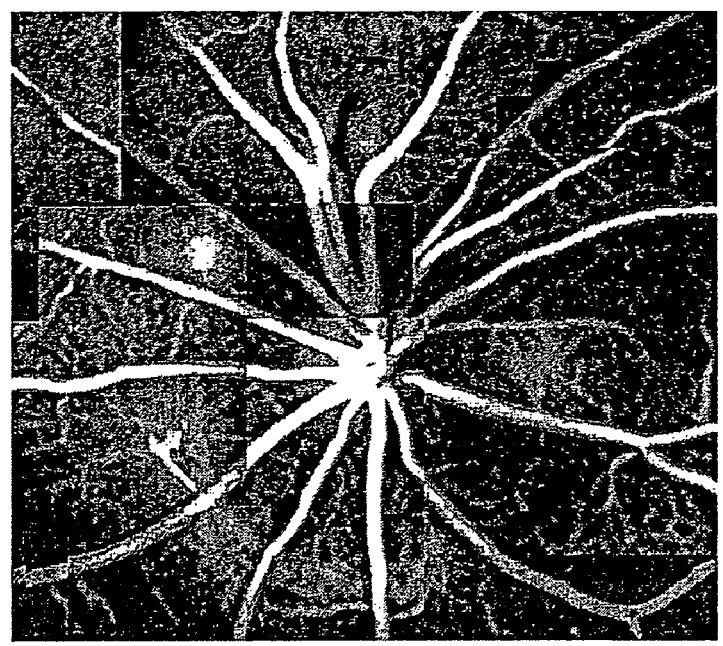

HDP-P-Ara G intravitreal toxicity and prophylactic treatment of rat CNV: After intravitreal injection, the drug formed a depot in the vitreous cavity with clear vitreous else where. The drug depot was observable for 2 weeks with the low dose (25 µg/eye) and for 4 to 5 weeks with the high dose (125 µg/eye). No toxicity was observed except for the local retinal toxicity that presented as a local retinal disturbance of fundus pigmentation where the drug depot touched the retina in the eyes with high doses (FIG. 7a). ERGs were normal in all eyes including the ones with local retinal toxicity (data not shown). Pathology study showed no toxicity in the eyes with 25 µg intravitreal injections. In the eyes with 125 µg intravitreal injections, localized retinal structural disturbance and proliferation or hypertrophy of retinal pigment epithelium were noticed (FIG. 7b). The retina was normal elsewhere. The prophylactic treatment for laser induced rat CNV revealed that 40% of the burns were actively leaking in the treated eyes versus 66% in the control eyes (p=0.009, paired t-Test). The drug led to a 39% reduction of CNV formation in this rat CNV model, judged by fluorescein angiograph (FIG. 8a, 8b).

Ara-G has been used as an antiproliferative agent to treat human leukemia and lymphoma.[11,12] Ara-G can cause apoptosis of fast growing cells by incorporating into the cell's DNA to inhibit the proliferation.[13] Normal cells in the retina are differentiated cell populations and are not sensitive to Ara-G. In contrast, abnormal proliferating cells in proliferative vitreoretinopathy experience vigorous DNA synthesis and are sensitive to Ara-G. The lipid prodrug of Ara-G was chosen to be useful to treat proliferative vitreoretinopathy or other intraocular proliferating disorders. After the crystalline HDP-P-Ara G intravitreal injection, a drug depot was formed in the inferior vitreous cavity. No intraocular drug toxicity was observed except for the local retina contact induced retinal toxicity from the high dose injections. It was hypothesized that the local retinal toxicity could be eliminated by using small crystalline particles, especially when used in a human eye with a much larger vitreous volume than rabbit (4 ml in human eye versus 1.4 ml in rabbit eye). To quickly gather the therapeutic data of this new compound on proliferation, 3 μg of HDP-P-Ara G (equivalent to 75 μg in the rabbit eye [(25+125)/2]) was injected into the right eye of each rat 3 days before induction of CNV by laser. The drug led to a 39% reduction of leaking laser burns in this CNV rat model (39% versus 66%, p=0.009). In addition, this dose did not cause any retinal toxicity including local retinal toxicity in the rat eyes. HDP-P-Ara G could be useful for prevention or treatment of the devastating sight-threatening eye disease, age related macular degeneration.

REFERENCES

1. Barza M. Factors affecting the intraocular penetration of antibiotics: the influence of route, inflammation, animal species and tissue pigmentation. *Scand J Infect Dis.* 1978; 14:151-159.
2. Cheng L, Hostetler K Y, Chaidhawangul S, Gardner M F, Beadle J R, Toyoguchi M, Bergeron-Lynn G, Freeman W R. Treatment or prevention of herpes simplex virus retinitis with intravitreally injectable crystalline 1-O-hexadecyl-propanediol-3-phospho-ganciclovir. *Invest Ophthalmol Vis Sci.* 2002; 43:515-21.
3. Bischofberger N, Hitchcock M J, Chen M S, Barkhimer D B, Cundy K C, Kent K M, Lacy S A, Lee W A, Li Z H, Mendel D B, et al. 1-[((S)-2-hydroxy-2-oxo-1,4,2-dioxaphosphorinan-5-yl)methyl] cytosine, an intracellular prodrug for (S)-1-(3-hydroxy-2-phosphonylmethoxypropyl) cytosine with improved therapeutic index in vivo. *Antimicrob Agents Chemother.* 1994; 38:2387-91.
4. Desideri N, Conti C, Mastromarino P, Mastropaolo F. Synthesis and anti-rhinovirus activity of 2-styrylchromones. *Antivir Chem. Chemother.* 2000; 11:373-81.
5. Beadle J R, Hartline C, Aldern K A, Rodriguez N, Harden E, Kern E R, Hostetler K Y. Alkoxyalkyl esters of cidofovir and cyclic cidofovir exhibit multiple-log enhancement of antiviral activity against cytomegalovirus and herpes virus replication in vitro. *Antimicrob Agents Chemother.* 2002; 46:2381-6.
6. Cheng L, Hostetler K Y, Gardner M F, Avila C P, Jr., Bergeron-Lynn G, Keefe K S, Wiley C A, Freeman W R. Intravitreal toxicology in rabbits of two preparations of 1-O-octadecyl-sn-glycerol-3-phosphonoformate, a sustained-delivery anti-CMV drug. *Invest Ophthalmol Vis Sci.* 1999; 40:1487-95.
7. Cheng L, Hostetler K Y, Chaidhawangul S, Gardner M F, Ozerdem U, Bergeron-Lynn G, Mach-Hofacre B, Mueller A J, Severson G M, Freeman W R. Treatment of herpes retinitis in an animal model with a sustained delivery antiviral drug, liposomal 1-O-octadecyl-SN-glycerol-3-phosphonoformate. *Retina.* 1999; 19:325-31.
8. Lim J I, Anderson C T, Hutchinson A, Buggage R R, Grossniklaus H E. The role of gravity in gentamicin-induced toxic effects in a rabbit model. *Arch Ophthalmol.* 1994; 112:1363-7.
9. Cheng L, Hostetler K Y, Toyoguchi M, Beadle J R, Rodanant N, Gardner M F, Aldern K A, Bergeron-Lynn G, Freeman W R. Ganciclovir release rates in vitreous from different formulations of 1-O-hexadecylpropanediol-3-phospho-ganciclovir. *J Ocul Pharmacol Ther.* 2003; 19:161-9.
10. Cundy K C, Lynch G, Shaw J P, Hitchcock M J, Lee W A. Distribution and metabolism of intravitreal cidofovir and cyclic HPMPC in rabbits. *Curr Eye Res.* 1996; 15:569-76.
11. Aldern K A, Ciesla S L, Winegarden K L, Hostetler K Y. Increased antiviral activity of 1-O-hexadecyloxypropyl-[2-(14)C]cidofovir in MRC-5 human lung fibroblasts is explained by unique cellular uptake and metabolism. *Mol. Pharmacol.* 2003; 63:678-81.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the claims.

What is claimed is:

1. A method for treating herpes simplex virus-1 (HSV-1) or cytomegalovirus (CMV) retinitis comprising intravitreally injecting a suspension of particles of 1-O-hexadecylcycloxypropyl-cyclic-cidofovir (HDP-cCDV) or particles of hexadecyloxypropyl-3-phosphoganciclovir (HDP-P-GCV) to the eye, wherein the HDP-cCDV and the HDP-P-GCV particles have a size of about 10 nm to 100,000 nm and wherein the particles are not liposomes.

2. The method of claim 1, wherein the particles of HDP-cCDV and the particles of HDP-P-GCV are in amorphous forms and/or crystalline forms.

3. The method of claim 1, wherein the particles of HDP-cCDV and the particles of HDP-P-GCV are in crystalline form.

4. The method of claim 1, wherein the particles of HDP-cCDV and the particles of HDP-P-GCV are in amorphous form.

5. A method for the slow-release delivery of 1-O-hexadecyloxypropyl-phospho-arabinofuranosyl-guanosine (HDP-P-Ara-G), 1-O-hexadecylcycloxypropyl-cyclic-cidofovir (HDP-cCDV) or hexadecyloxy-propyl-3-phospho-ganciclovir (HDP-P-GCV) to the eye, comprising intravitreally injecting a suspension of particles of HDP-P-Ara-G, or particles of HDP-cCDV or particles of HDP-P-GCV to the eye, wherein the HDP-cCDV and the HDP-P-GCV particles have a size of about 10 nm to 100,000 nm and wherein the particles are not liposomes.

6. A method for increasing residence time of 1-O-hexadecylcycloxypropyl-phospho-arabinofuranosylguanosine (HDP-P-Ara-G 1-O-hexadecylcycloxypropyl-cyclic-cidofovir (HDP-cCDV) or hexadecyloxypropyl-3-phospho-ganciclovir (HDP-P-GCV) in the eye, comprising intravitreally injecting a suspension of particles of HDP-P-Ara-G, particles of HDP-P-cCDV or particles of HDP-GCV to the eye, wherein the particles have a size of about 10 nm to 100,000 nm and wherein the particles are not liposomes.

* * * * *

UNITED STATES PATENT AND TRADEMARK OFFICE
CERTIFICATE OF CORRECTION

| | | |
|---|---|---|
| PATENT NO. | : 8,017,135 B1 | Page 1 of 1 |
| APPLICATION NO. | : 10/770885 | |
| DATED | : September 13, 2011 | |
| INVENTOR(S) | : Hostetler et al. | |

It is certified that error appears in the above-identified patent and that said Letters Patent is hereby corrected as shown below:

Please amend the paragraph beginning on Line 14 of Column 1 and ending on Line 18 of Column 1 as follows:

This invention was made ~~in part~~ with government support under Grant Nos. EY07366 and EY11832, awarded by the National Institutes of Health, National Eye Institute. The ~~United States~~ government has~~may have~~ certain rights in the~~this~~ invention.

Signed and Sealed this

Eleventh Day of October, 2011

David J. Kappos
*Director of the United States Patent and Trademark Office*